United States Patent [19]
Carlson et al.

[11] Patent Number: 5,814,058
[45] Date of Patent: Sep. 29, 1998

[54] METHOD AND APPARATUS EMPLOYING CONFORMABLE SLEEVE FOR PROVIDING PERCUTANEOUS ACCESS

[75] Inventors: John Carlson, Mountain View; Craig K. Tsuji, Santa Clara; Steven P. Masterson, San Francisco; Michael J. Orth, Morgan Hill, all of Calif.

[73] Assignee: Innerdyne, Inc., Sunnyvale, Calif.

[21] Appl. No.: 696,755

[22] Filed: Aug. 14, 1996

Related U.S. Application Data

[60] Continuation-in-part of Ser. No. 424,696, Apr. 19, 1995, which is a division of Ser. No. 26,922, Mar. 5, 1993, Pat. No. 5,431,676.

[51] Int. Cl.⁶ .................................................. A61B 17/00
[52] U.S. Cl. ........................................ 606/185; 606/191
[58] Field of Search ..................................... 604/104, 109, 604/164, 166, 171, 172, 264, 280, 281, 52, 53; 606/191, 198, 108; 600/201

[56] References Cited

U.S. PATENT DOCUMENTS

| | | |
|---|---|---|
| 668,879 | 2/1901 | Miller . |
| 1,213,001 | 1/1917 | Philips . |
| 1,248,492 | 12/1917 | Hill . |
| 2,548,602 | 4/1951 | Greenburg . |
| 3,509,883 | 5/1970 | Dibelius . |
| 3,545,443 | 12/1970 | Ansari . |
| 3,742,958 | 7/1973 | Rundles . |
| 3,789,852 | 2/1974 | Kim et al. . |
| 3,902,492 | 9/1975 | Greenhalgh . |
| 4,141,364 | 2/1979 | Schultze . |
| 4,411,655 | 10/1983 | Schreck . |
| 4,479,497 | 10/1984 | Fogarty et al. . |
| 4,581,025 | 4/1986 | Timmermans . |
| 4,589,868 | 5/1986 | Dretler . |
| 4,601,713 | 7/1986 | Fugua . |
| 4,716,901 | 1/1988 | Jackson et al. . |
| 4,738,666 | 4/1988 | Fuqua . |
| 4,739,762 | 4/1988 | Palmaz . |
| 4,772,266 | 9/1988 | Groshong . |
| 4,798,193 | 1/1989 | Giesy et al. . |
| 4,846,791 | 7/1989 | Hattler et al. . |
| 4,865,593 | 9/1989 | Ogawa et al. . |
| 4,888,000 | 12/1989 | McQuilkin et al. . |
| 4,896,669 | 1/1990 | Bhat et al. . |
| 4,899,729 | 2/1990 | Gill et al. . |
| 4,921,479 | 5/1990 | Grayzel . |
| 4,955,895 | 9/1990 | Sugiyama et al. . |
| 4,972,827 | 11/1990 | Kishi et al. . |
| 4,986,830 | 1/1991 | Owens et al. . |
| 5,116,318 | 5/1992 | Hillstead . |
| 5,122,122 | 6/1992 | Allgood . |
| 5,139,511 | 8/1992 | Gill et al. . |
| 5,158,545 | 10/1992 | Trudell et al. . |
| 5,183,464 | 2/1993 | Dubrul et al. . |
| 5,201,756 | 4/1993 | Horzewski et al. . |
| 5,250,033 | 10/1993 | Evans et al. . |
| 5,275,611 | 1/1994 | Behl . |
| 5,312,360 | 5/1994 | Behl . |
| 5,320,611 | 6/1994 | Bonutti et al. . |
| 5,407,430 | 4/1995 | Peters . |
| 5,431,676 | 7/1995 | Dubrul et al. . |

FOREIGN PATENT DOCUMENTS

| | | |
|---|---|---|
| WO 94/20026 | 9/1994 | WIPO . |
| WO 95/30374 | 11/1995 | WIPO . |

*Primary Examiner*—Michael Buiz
*Assistant Examiner*—William Lewis
*Attorney, Agent, or Firm*—Townsend and Townsend and Crew LLP

[57] ABSTRACT

Methods and systems for introducing articles and surgical instruments to target body cavities utilize conformable sleeves which are percutaneously positioned within the cavity. Articles may then be passed directly through the conformable sleeve, without use of a rigid cannula, either by pushing the articles inwardly through the sleeve using an introducer or pulling the articles inwardly through the sleeve using a tapered carrier. Surgical instruments are also passed directly inwardly through the sleeve. Such systems and methods may be used in a variety of minimally invasive surgical procedures.

63 Claims, 11 Drawing Sheets

METHOD AND APPARATUS EMPLOYING CONFORMABLE SLEEVE FOR PROVIDING PERCUTANEOUS ACCESS

The present application is a continuation-in-part of application Ser. No. 08/424,696, filed on Apr. 19, 1995, which was a division of application Ser. No. 08/026,922, filed on Mar. 5, 1993, which has now issued as U.S. Pat. No. 5,431,676. The full disclosures of each of these patent applications and patent are incorporated herein by reference.

BACKGROUND OF THE INVENTION

1. Field of the Invention

The present invention relates generally to apparatus and methods for providing percutaneous access to an internal operative site during a surgical procedure. More particularly, the present invention relates to introducing articles and surgical instruments through a conformable sleeve which has been positioned in a percutaneous penetration, where the article or instrument temporarily expands the sleeve as the article or instrument is introduced.

Conventional minimally invasive surgical procedures rely on obtaining percutaneous access to an internal surgical site using small-diameter access tubes (typically 5 to 12 mm), usually referred to as cannulas, which penetrate through the skin and which open to the desired surgical site. A viewing scope is introduced through one such cannula, and the surgeon operates using instruments introduced through other appropriately placed cannulas while viewing the operative site on a video monitor connected to the viewing scope. The surgeon is able to perform a wide variety of surgical procedures requiring only several 5 to 12 mm punctures at the surgical site. Patient trauma and recovery time are thus greatly reduced.

Particular minimally invasive surgical procedures are often referred to based on the type of scope used to view the region of the body which is the operative site. Thus, procedures in the abdominal area, which rely on a "laparoscope" for viewing, are referred to as laparoscopic procedures. In such laparoscopic procedures, the patient's abdominal region is typically insufflated (filled with pressured carbon dioxide or nitrogen gas) to raise the abdominal wall and create sufficient operating space to perform a desired procedure. The cannulas used in laparoscopic procedures must therefore include a valve at their proximal end to allow passage of the scope or surgical instruments while inhibiting leakage of the insufflating gas. It has also been proposed to perform laparoscopic procedures by mechanically expanding the abdomen rather than using insufflation.

Other minimally invasive surgical procedures include "thoracoscopic" procedures performed in the region of the chest, "arthroscopic" procedures performed in body joints, particularly the knee, gynecological laparoscopic procedures, and "endoscopic" surgical procedures performed in various regions of the body, typically with a flexible scope. These latter procedures do not normally employ pressurization and the cannulas used generally do not include pressure valves at their proximal ends.

Until now, most cannulas have comprised rigid structures formed from stainless steel, hard plastics, or other non-compliant materials. The cannulas are usually introduced using stylets, referred to as trocars, having sharpened distal ends which create a rather large wound as they are introduced through tissue. Once introduced, such cannulas provide a fixed-diameter access lumen, usually in the 5 mm to 12 mm range set forth above. The lumen is non-collapsible, and surgical instruments and articles which are smaller than the lumen diameter may be freely introduced through the cannula.

While the advent of minimally invasive surgical procedures has been nothing less revolutionary, the use of trocars for introducing fixed-diameter cannulas suffers from certain drawbacks. First, conventional trocar/cannula assemblies provide little or no size flexibility. Once a cannula has been percutaneously inserted, it has been difficult or impossible to change the size of the cannula. Thus, the treating physician must choose between either introducing an "oversized" cannula to begin with (thus subjecting the patient to unnecessary trauma associated with the larger trocar size) or risk the need to introduce an additional trocar/cannula assembly later in the procedure if it appears necessary that a larger access lumen is needed. A second related problem arises from the limited range of cannula sizes available, typically one 5 mm, 10 mm, and 12 mm diameters are utilized. The need to accommodate the surgical instrument or article being introduced requires that the next larger size of cannula be employed. Frequently, this will require introduction of a trocar/cannula assembly which is larger than that actually required to accommodate the instrument or article, again subjecting the patient to unnecessary trauma. Third, conventional trocar/cannula assembly are somewhat complex and require significant structure to maintain the access lumen.

It would therefore be desirable to achieve more flexibility and reduced patient trauma in providing percutaneous access for various minimally invasive surgical procedures. U.S. Pat. No. 5,431,676, which issued from the grandparent of the present application, overcomes some but not all of the disadvantages described above. U.S. Pat. No. 5,431,676, describes a radially expandable dilator system comprising a conformable sleeve referred to as a dilation tube, and an expansion member comprising a rigid outer tube (or cannula) and an inner rod. The conformable sleeve may be percutaneously introduced using a needle and, after removing the needle, left in place in a radially collapsed condition. The conformable sleeve is then expanded by introducing the expansion member inwardly through a lumen of the sleeve. After the expansion member is fully inserted, the inner rod is removed, leaving the outer sleeve or cannula in place to provide the desired percutaneous access lumen. The radially expanding dilator system is particularly advantageous since it reduces the initial trauma cannula and facilitates subsequent exchange of different-sized cannulas. Such exchange may be conveniently accomplished by withdrawing a first cannula sleeve, resulting in radial collapse of the conformable sleeve. A second expansion member, having a larger or smaller cannula sleeve may be then reintroduced through the collapsed conformable sleeve. There is thus no need to make a second penetration to provide a cannula having a larger or smaller size.

Although a significant improvement over conventional trocar/cannula assemblies as described above, the radially expandable dilating system of U.S. Pat. No. 5,431,676, still suffers from certain drawbacks. Most importantly, the cannula sleeve which provides the access lumen is rigid and cannot accommodate oversized instruments or articles. The commercially available dilator system employing the technology of U.S. Pat. No. 5,431,676, sold as the STEP™ Cannula Obturator Radially Expandable Sleeve, is presently available with only three cannula diameters. Thus, it will generally be necessary to utilize the next larger cannula size, frequently resulting in slight over dilation of the percutaneous tissue penetration. While this is less of a problem with the STEP™ system then with conventional trocar/cannula systems (which cut the tissue with the trocar tip), it is still undesirable.

For these reasons, it would be desirable to provide still further improved percutaneous access systems which overcome some or all of the drawbacks described above. In particular, it would be desirable to provide percutaneous access systems which rely on initial introduction of a small-diameter access tube which can expand to accommodate a wide variety of surgical instruments and articles without the need to over dilate or over expand the percutaneous tissue penetration. It would be further desirable if such systems could accommodate instruments and articles having irregular shapes, where the percutaneous tissue penetration is stretched by an amount just sufficient to accommodate the periphery of the instrument or article. Thus, it would be desirable to have the percutaneous access sleeve conform to an instrument and/or article as the instrument and/or article is being introduced therethrough. Such percutaneous access systems should function well with both surgical instruments and articles, should be relatively inexpensive to manufacture, and should provide for reliable percutaneous access with minimum patient trauma.

2. Description of the Background Art

U.S. Pat. No. 5,431,676, has been described above. WO 94/20026, published in September 1994, has a disclosure equivalent to U.S. Pat. No. 5,431,676. U.S. Pat. No. 5,183,464, assigned to the assignee of the present invention, describes a radially expandable dilator including an elongate dilation tube which receives an elongate expansion tube. European Patent Application 385 920 describes a variable diameter braid structure intended for capturing and removing stenotic material from blood vessels. U.S. Pat. No. 5,122,122, describes a trocar sleeve having a malecot structure at its distal end. Trocars for use in laparoscopic procedures are commercially available from suppliers such as United States Surgical Corp. Norwalk, Connecticut; Endomed division of Cooper Surgical, Inc., Shelton, Conn.; and Dexide Inc., Fort Worth, Tex.

U.S. Pat. No. 4,738,666, describes an expandable catheter having an external sheath which is perforated to facilitate removal as the catheter is being expanded. U.S. Pat. No. 4,601,713, describes a variable diameter catheter having an inflatable retention balloon at its distal end. The catheter is introduced with an internal stylet which holds the catheter in a collapsed (reduced diameter) configuration. Removal of the stylet allows the catheter to expand. U.S. Pat. No. 4,141,364, describes an expandable endotracheal tube which is inserted in a collapsed configuration and springs back to an expanded configuration when air is introduced. Inflatable dilator apparatus are described in U.S. Pat. Nos. 4,589,868 and 2,548,602. Catheters having expandable structures are described in U.S. Pat. Nos. 4,986,830; 4,955,895; 4,896,669; 4,479,497; and 3,902,492.

U.S. Pat. No. 4,772,226, describes a dilator/sheath assembly that may be passed over an in-dwelling guidewire in order to enlarge an access hole, with entry of the sheath further enlarging the hole. U.S. Pat. No. 1,213,001, describes a trocar and cannula assembly which includes an intermediate tube to form a three-piece structure. U.S. Pat. No. 3,742,958, discloses a cannula having an axial slot to allow the cannula to be stripped from a working catheter which has been introduced through the cannula. U.S. Pat. Nos. 4,888,000; 4,865,593; 4,581,025; 3,545,443; and 1,248,492, each describe devices suitable for percutaneous penetration of a body cavity, blood vessel, or solid tissue. The disclosures of each of the U.S. Patents cited in this paragraph are hereby incorporated herein by reference.

U.S. Pat. No. 4,899,729, describes an expansible cannula which includes a coiled conical sheath which can be percutaneously introduced and thereafter expanded by advancing an internal cylinder. U.S. Pat. No. 4,716,901 discloses an expandable trocar (not including a trocar valve) comprising a pair of opposed components having sharpened distal tips and covered by an elastic sleeve over a proximal portion thereof. U.S. Pat. No. 4,846,791, describes a multi-lumen catheter which includes an elastic outer sleeve and an internal divider which, when inserted, expands the sleeve. See also U.S. Pat. Nos. 668,879; 3,789,852; 4,411,655; 4,739,762; 4,798,193; 4,921,479; 4,972,827; 5,116,318; and 5,139,511, which were made of record in U.S. Pat. No. 5,183,464, assigned to the assignee of the present invention.

A dilator assembly including a guide member having an anchor at its distal end is described in U.S. Pat. Nos. 5,316,360 and 5,275,611, assigned to the assignee of the present invention, the disclosures of which are incorporated herein by reference. A peel away sheath s described in U.S. Pat. No. 5,250,033, assigned to the assignee of the present invention, the disclosure of which is incorporated herein by reference.

SUMMARY OF THE INVENTION

According to the present invention, approved methods and apparatus are provided for accessing a target site in a body cavity. A first method according to the present invention comprises percutaneously inserting a conformable sleeve to the target site. An article is then passed from outside the body through a lumen of the conformable sleeve to the target site. Passage of the article will radially expand the lumen of the sleeve as the article advances therethrough. Advantageously, the sleeve need expand only enough to accommodate the article, reducing trauma to the patient to a minimum. After the article has reached the interior end of the sleeve, it may be removed and positioned within the body cavity as desired.

The articles may be passed through the conformable sleeve in two different ways. First, the articles may be mounted onto a shaft, and the shaft used to advance the article through the conformable sleeve so that the article is pushed into the body cavity from the distal end of the conformable sleeve. In such cases, the article will usually be removed from the shaft (optionally using an instrument passed through a second conformable sleeve according to another aspect of the present invention), and the shaft then withdrawn outwardly from the conformable sleeve so that the sleeve collapses back down to its narrow profile configuration. The conformable sleeve will then be ready for introducing additional articles, instruments, or the like, or may be withdrawn from the percutaneous tissue penetration, leaving a wound which is generally less extensive than would be the case had a conventional trocar/cannula assembly been used.

Articles may also be introduced using a second general approach which relies on percutaneously inserting a grasping element through a separate location to the body cavity. The grasping element may be conventional laproscopic surgical graspers or any other elongated device capable of engaging and capturing the article, or an associated article carrier, as described below. Usually, the article will be placed in a tapered carrier having a capture element at its narrow diameter end and an opening at its large diameter end. The article may be inserted through the opening, and the carrier introduced inwardly through the conformable sleeve until the capture element extends from the inner end of the conformable sleeve into the body cavity. The graspers may then be used to capture the capture element and pull the tapered carrier through the conformable sleeve into the body cavity. The article may then be removed from the tapered carrier, typically through the opening. The carrier may be a rigid conical structure, or may be a more flexible structure which wraps around the article to define a generally tapered or conical configuration to facilitate passage through the conformable sleeve.

In a second aspect of the method of the present invention, elongate instruments may be used for performing procedures through conformable sleeves. The conformable sleeve is first percutaneously inserted to a target site within a body cavity. The elongate instrument is positioned through a central lumen of the conformable sleeve so that an effector at the distal end of the instrument is positioned at the target site. The user manipulates the instrument with a proximal handle which remains outside the body in order to perform the procedure. In a least complicated embodiment, the effector will be a paddle or other passive element, and the instrument is deployed by simply engaging it against a tissue structure and manipulating the instrument to retract or otherwise move the tissue structure in a desired manner. In more common embodiments, the manipulating step will further comprise actuating an actuator on the handle to actively deploy the end effector in some manner. The end effectors may be virtually any conventional surgical instrument, including graspers, scissors, forceps, needle drivers, electrosurgical probes, staplers, viewing scopes, irrigation devices, suction devices, and the like. Graspers introduced through a conformable sleeve may be used in conjunction with a second conformable sleeve in order to introduce articles using the tapered carrier of the present invention, as described above.

The present invention further provides systems for percutaneously introducing articles according to the method described above. Systems comprise an introducer shaft having a proximal end, a distal end, and a storage location near the distal end for removably carrying the article. The system further comprises an elongate conformable sleeve having a proximal end, a distal end, and a lumen which slidably receives the introducer shaft. The sleeve will have a compliant or elastic structure so that its cross-section (periphery) will collapse when positioned in a constrictive percutaneous penetration (i.e., as a result of the radially inward force created by the tissue surrounding the penetration) but will expand as the introducer shaft (usually carrying the article) is passed through the lumen.

Preferably, the introducer shaft will have a tapered distal end to facilitate passage through the lumen of the elongate conformable sleeve. The storage location is usually recessed behind the tapered distal end, and in most instances the article will remain behind the tapered distal end and will pass through the expanded lumen created as the shaft is introduced through the conformable sleeve. It will be appreciated, however, that a particular advantage of the present invention is that the article can have a larger and/or irregular peripheral configuration which extends beyond the "envelope" created by the tapered distal tip of the shaft and further that the shaft need not always be tapered. The conformable sleeve will be able to accommodate and pass a variety of shapes and sizes which would not be possible with the rigid cannulas of the prior art.

In a specific configuration, usable with surgical meshes and other articles that can be confined within limited areas, introducer shaft will include a tubular cover over the storage location. The tubular cover may have an aperture or may be retractable relative to the shaft in order to permit loading and/or unloading of the article from therein. Use of the tubular cover will facilitate introduction and withdrawal of the shaft assembly, but may limit the ability to introduce over-sized or irregularly shaped articles.

The elongate sleeve will typically have a length in the range from about 5 cm to 20 cm, preferably from 5 cm to 10 cm, and a maximum internal diameter when radially expanded in the range from 1 mm to 18 mm, preferably from 5 mm to 12 mm. The introducer shaft will usually have a length which is at least 5 cm longer than the length of the elongate sleeve.

The article may be provided as part of the system, typically being packaged therewith within a sural bag, pouch, or other conventional package. Alternatively, the system may be provided without the article, and conventional surgical articles, such as surgical meshes, may be introduced or loaded into the shaft in the operating room or other sterile environment.

The present invention further comprises the introducer shaft itself for use in combination with a conformable sleeve. The introducer shaft will comprise a tapered tip at the distal end of the shaft, where the tapered tip defines a recessed region on the shaft for receiving an article to be delivered by the shaft through the conformable sleeve. The apparatus will usually further comprise a handle at a proximal end of the shaft to facilitate manipulation. Preferably, the shaft further comprises a tubular cover which extends proximally from the tapered distal tip, wherein the recessed region for receiving the article is disposed within the cover. The tubular cover may have an aperture for accessing the article, including inserting and removing the article from the recessed storage location. Alternatively, or in addition, the tubular cover may be retractable relative to the distal tip to expose the recessed region for loading and unloading their article. Usually, the shaft will have a length in the range from 10 cm to 25 cm and a maximum width, usually a diameter for circular cross-sections, in the range from 1 mm to 18 mm, preferably from 5 mm to 12 mm.

Apparatus according to the present invention still further comprise a system including both a tapered carrier and an elongate conformable sleeve, typically sold together in a sterile package. The tapered carrier is generally as described above in connection with the method of the present invention, having a hollow body, a tapered distal end, and an opening at a proximal end to permit loading and unloading of the article within the tapered carrier. The elongate conformable sleeve has a proximal end, a distal end, and lumen which slidably receives the tapered carrier. The sleeve has an elastic or compliant structure so that its cross-section will collapse when positioned in a constrictive percutaneous penetration but will expand as the tapered carrier is passed through the lumen. Usually, the capture element is provided at the distal end of the tapered carrier (i.e. the end which passes inwardly through the lumen of the elongate conformable sleeve), where the capture element will enter the body cavity first so that it may be grasped by separately introduced graspers to pull the tapered carrier into the body cavity. The tapered carrier may be rigid (non-collapsible) or may be a relatively compliant or flexible material which conforms to the article. Typically, the exterior of the tapered carrier will be lubricous in order to enhance introduction through the elongate sleeve. The tapered carrier may be packaged together with the article to be introduced, e.g. a surgical mesh. The dimensions of the tapered carrier will be sufficient to accommodate the article to be introduced, typically having a length in the range from 5 cm to 20 cm and a maximum width (in the case of rigid carriers) at its proximal end in the range from 5 mm to 18 mm.

DESCRIPTION OF THE SPECIFIC EMBODIMENTS

Figure 1:
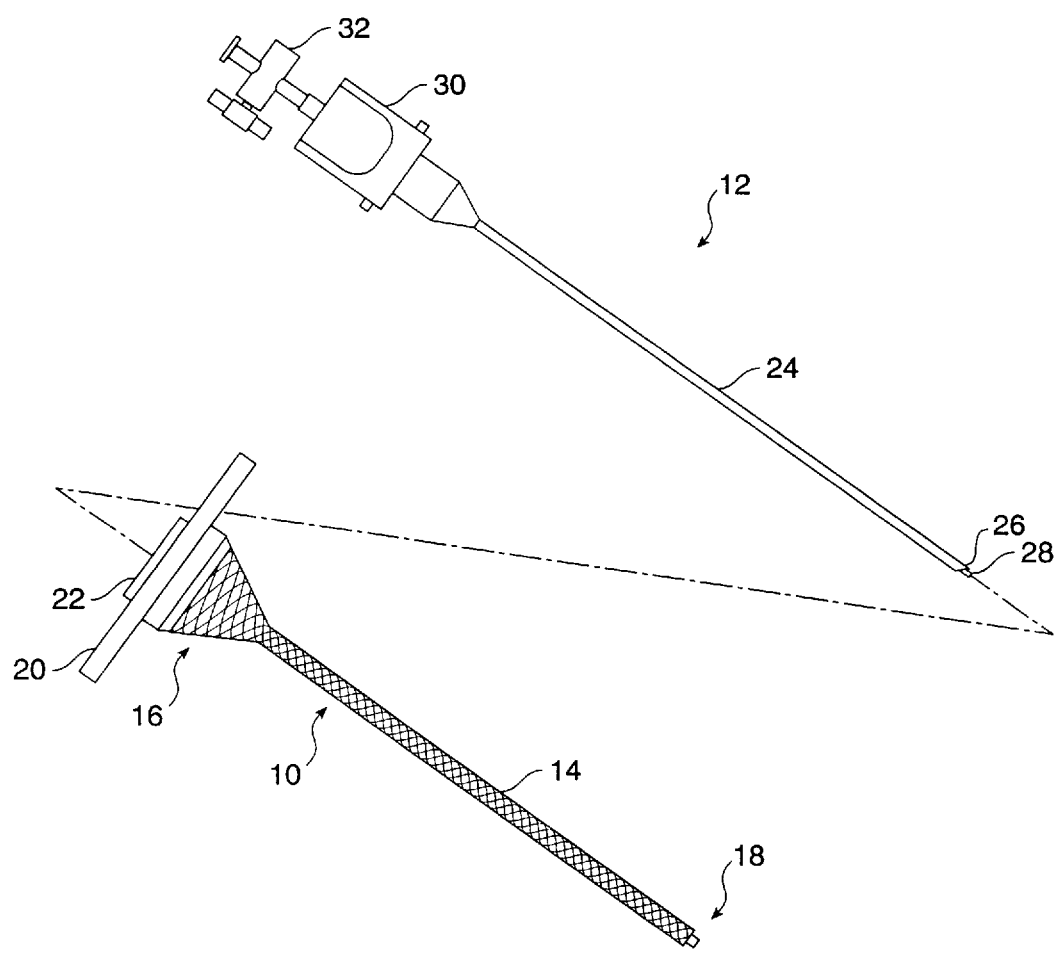
FIG. 1 illustrates a conformable sleeve and a pneumoperitoneum needle which are useful in the methods and systems of the present invention.

Systems according to the present invention will comprise a conformable sleeve and at least one additional component for passing an article through the sleeve into the target body cavity. In a first embodiment, the additional component is an elongate introducer which carries the article near its distal end and which is used to push the article inwardly through the sleeve. In the second embodiment, the additional component is a carrier which can be grasped from within the body cavity and pulled inwardly through the sleeve. The conformable sleeve may also be used by itself for the direct introduction of laproscopic and other surgical instruments without use of a separate cannula. In all cases, the conformable sleeve will be radially expanded only to extend necessary to accommodate the article, introducer, carrier, and/or instrument. There is no need to utilize a rigid cannula or to leave such a cannula in place for subsequent use. The conformable sleeve of the present invention will accommodate both articles and instruments of widely different sizes without the need to exchange cannulas to position a cannula having a different lumen size.

The conformable sleeve comprises a radially expandable tubular sheath having a proximal end, a distal end, and an axial lumen extending from the proximal end to the distal end. Usually, a handle is provided at the proximal end of the tubular sheath so that the sleeve can be manually held during use, e.g. as the article or instrument is being inserted therethrough. The tubular sheath will have a compliant or elastic structure which permits expansion from an initial low profile (radially collapsed) diameter configuration to a larger size necessary to accommodate passage of the article or instrument being inserted therethrough. Usually, the tubular sheath will be at least partly elastic so that the cross-section will tend to close after it has been initially stretched to pass the article or instrument. The sheath could, however, be non-elastic, plastically deformable, or have an otherwise non-resilient structure, in which case the cross-section of the sheath will still close in response to a constrictive or closing force applied by the surrounding percutaneous tissue penetration after the article or instrument has been removed.

It will be appreciated that a primary requirement of the tubular sheath of the conformable sleeve is to permit passage of articles and instruments through percutaneous penetrations having smaller sizes than the article or instrument. The tubular sheath will permit passage of such articles and instruments without transferring sufficient axial forces to cause separation of tissue layers. The forces resulting from introduction of the article or instrument will be directed primarily in a radial direction so that the percutaneous tissue penetration is radially expanded. Since the articles or instruments may be passed directly through the lumen of the sheath (or articles may be passed using introducers or carriers having a size which is just large enough to accommodate the article), the degree of radial expansion will also be limited.

A preferred radially expandable tubular sheath comprises an expandable tubular braid which is initially in an elongated, narrow-diameter configuration. The braid may be open, but will often be laminated or covered with a coating or layer of elastic or plastically deformable material, such as silicone rubber, latex, polyethylene, C-flex, or the like. The tubular braid is percutaneously introduced in its narrow-diameter configuration, and thereafter radially expanded using an elongate expansion member, as described in more detail hereinafter. The tubular braid is preferably formed as a mesh of individual non-elastic filaments (e.g., composed of polyamide fiber (Kevlar®, DuPont), stainless steel, or the like) so that radial expansion causes axial shortening of the braid. Such axial shortening as the braid filaments are radially penetrated into the surrounding tissue helps anchor the dilation member in place within the patient's tissue and helps seal the exterior of the sheath against the tissue. Such a firmly anchored and gas-tight seal is a particular advantage in laproscopic procedures.

The braid may be of conventional construction, comprising round filaments, flat or ribbon filaments, square filaments, or the like. Non-round filaments may advantageously reduce the axial force require to provide radial expansion. The filament width or diameter will typically be from about 0.002 inch to 0.25 inch, usually being from about 0.005 to 0.010 inch. Suitable braids may be obtained from a variety of commercial suppliers, such as Bently-Harris, Lionville, Pa.; Manville Sealing Components, Denver, Colo.; and 3M Ceramic Materials, St. Paul, Minn. A particularly suitable braid is available under the tradename Exando® PT from Bently-Harris.

The elongate conformable sleeve may optionally further include a removable cover covering the tubular braid of the sheath. The cover is usually composed of a lubricous material, such as a thin-walled flexible plastic, such as polyethylene, tetrafluoroethylene, fluorinated ethylenepropylene, and the like. The cover protects the tubular braid during initial insertion of the dilation member, but may be removed from the braid after the dilation member is in place. Preferably, the cover will be weakened along an axial line to facilitate splitting of the cover at some point during the procedure. Such removable covers will usually be employed only if the tubular braid does not itself include an elastic or deformable layer secured to the braid filament material. Such conformable sleeve structures are described in detail in U.S. Pat. No. 5,431,676, the full disclosure of which has been previously incorporated herein by reference. Such conformable sleeves are also commercially available from Innerdyne Medical, Sunnyvale, Calif. 94089, as part of the STEP™ Cannula Obturator and Radially Expandable Sleeve system.

The conformable sleeve may be introduced through a previously formed percutaneous penetration formed using a needle, stylet, or other conventional penetrating device. More usually, however, the conformable sleeve will be self-introduced using a puncturing element which is temporarily or permanently affixed at the distal end of the sleeve. Preferably, the puncturing element will comprise a separate elongate penetrating element which is received in an axial lumen of the radially expandable tubular sheath, while the sheath is in its axial elongate configuration. The penetrating element includes a sharpened distal tip which extends distally beyond the distal end of the tubular sheath and optional cover, thus facilitating penetration of the conformable sleeve through the tissue.

In an exemplary embodiment, the penetrating element is a pneumoperitoneum needle which includes an obturator which is retractably mounted therein and which extends distally beyond the sharpened distal tip. The obturator is usually spring-loaded, and will thus automatically retract as the needle is advanced through tissue and encounters significant tissue resistance to puncture. The obturator will, however, extend distally beyond the sharpened distal tip to protect the patient from injury after the dilation member has entered the desired target location, such as within the insufflated region of the abdomen during laparoscopic procedure. Such needles are known as Veress needles and are commonly employed for insufflation in laparoscopic and other procedures. Such pneumoperitoneum needles may also be commercially obtained as part of the STEP™ system from Innerdyne Medical. The handle of the conformable sleeve will usually include an aperture or opening which is aligned with the axial lumen of the tubular sheath. Usually, the aperture will have a circular periphery which corresponds generally to the maximum expected expanded diameter of the tubular sheath. The aperture, however, could alternatively have an irregular shape intended to accommodate particular articles and/or instruments expected to be introduced through the sleeve. Optionally, a hemostasis valve could be provided within the aperture in order to inhibit loss of insufflation pressure when the sleeve is used in laproscopic procedures. As a further option, the handle could include a bayonet or other conventional fitting to permit mounting of valves, caps, a pneumoperitoneal needle (as is the case in the radially expandable sleeve of the STEP™ system), or the like.

Introducers according to the present invention will be used for carrying an article and pushing the article inwardly through the conformable sleeve to a target body cavity. The introducers will have an elongate, narrow profile geometry suitable for passing through the lumen of the conformable sleeve with minimum radial expansion thereof. Usually, a distal end of the introducer will be tapered to facilitate the inward penetration of the conformable sleeve. A recessed region will be located proximal to the taper for carrying the article. Several specific structures for introducers are described in detail in connection with FIGS. 2–4 below. It will be appreciated, however, that a wide variety of alternative structures may be developed for particular articles within the scope of the present invention.

Figure 6:
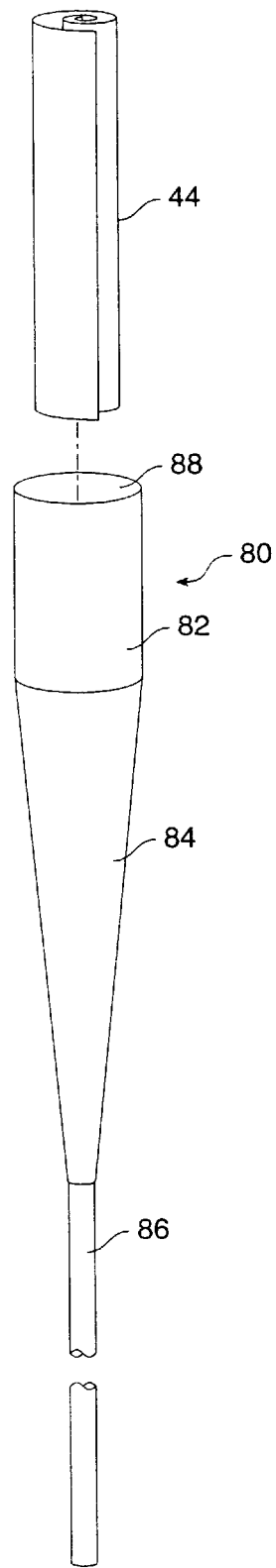
FIG. 6 illustrates a tapered carrier constructed in accordance with the principles of the present invention.

As an alternative to the use of elongate introducers, tapered carriers may be used to permit an article to be grasped from inside the body cavity and pulled into the body cavity. An exemplary rigid tapered carrier is illustrated in FIG. 6 below. It will be appreciated, however, that a wide variety of non-rigid and other carrier structures can be devised. The primary requirement of the carrier is that it provide a grasping element which can pass through the conformable sleeve and into the body cavity. The physician can then use conventional surgical graspers to capture the grasping element and pull the carrier and article through the conformable sleeve and into the body cavity, as described in more detail below in connection with FIGS. 7A and 7B.

Referring now to FIG. 1, a conformable sleeve 10 and pneumoperitoneum needle 12 which may be used in the methods and systems of the present invention are illustrated. The conformable sleeve 10 comprises a radially expandable tubular sheath 14 having a proximal end 16 and a distal end 18. The proximal end 16 is tapered radially outwardly in the proximal end and secured to a handle 20. An aperture in the handle 20 (not shown) is aligned with the expanded diameter of the proximal end 16 and includes a bayonet fitting 22 aligned with the aperture.

The radially expandable tubular sheath 14 comprises a braid covered by an elastic membrane, so that the braid and cover will expand as articles or instruments pass therethrough, but will thereafter radially close under the elastic force of the membrane. The conformable sleeve 10 as illustrated in FIG. 1 may be obtained commercially from Innerdyne Medical, Sunnyvale, Calif., as part of the STEP™ system.

The pneumoperitoneum needle 12 comprises a hypotube shaft 24 having a sharpened distal tip 26 and a spring-loaded obturator 28 which extends from the tip. The bayonet fitting 30 is disposed at a proximal end of the hypotube shaft 24 and a valve 32 is disposed on the fitting 30.

The pneumoperitoneum needle 12 may thus be mounted within the lumen of the conformable sleeve 12 with the fitting 30 secured within handle 20. The sharpened tip 26 and obturator 28 of the needle will extend distally from the distal end 18 of the conformable sleeve. In this way, the assembly of the conformable sleeve 10 and needle 12 may be directly introduced through a patient's skin (i.e. without the need of using a prior penetration) in order to form a percutaneous penetration to the target body cavity. After initial penetration, the pneumoperitoneum needle 12 could be used to provide for initial insufflation of the patient's body cavity, typically the abdomen for laparoscopic procedures. Often, however, the conformable sleeve 10 will be introduced in non-laproscopic procedures and/or after the procedure has been begun. In such cases, use of a peritoneum needle is not required. A more simple needle could be used in such circumstances, but inclusion of the obturator 28 is advantageous since it reduces the risk of injury from blind insertion of an unprotected needle tip.

Figure 2:
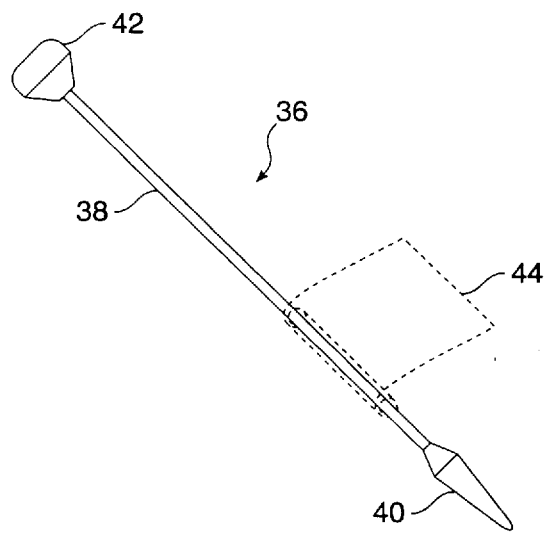
FIG. 2 illustrates a first embodiment of an introducer shaft constructed in accordance with the principles of the present invention.

Referring now to FIG. 2, a first embodiment of an introducer suitable for use in the method and systems of the present invention will be described. The introducer 36 comprises a shaft 38 which may comprise a stainless steel rod, hypotube, or the like. The tapered distal tip 40 secured to a distal end of the shaft and a handle 42 is secured to a proximal end of the shaft. The tapered distal tip 40 defines a recessed location proximal to the tip on the shaft 38 where a surgical mesh 44 or other article may be mounted for delivery through the conformable sleeve 10. It will be appreciated that the surgical mesh may be rolled directly onto the shaft 38 so that its profile is generally less than the maximum profile of the tapered distal tip 40. In this way, introduction of the distal tip 40 and the mesh 44 is facilitated as the tip temporarily opens the lumen of the conformable sleeve 10 so that the mesh may pass therethrough. Use of the introducer 10 for introducing the surgical mesh 44 will be described in greater detail below in connection with FIGS. 5A–5C.

Figure 3:
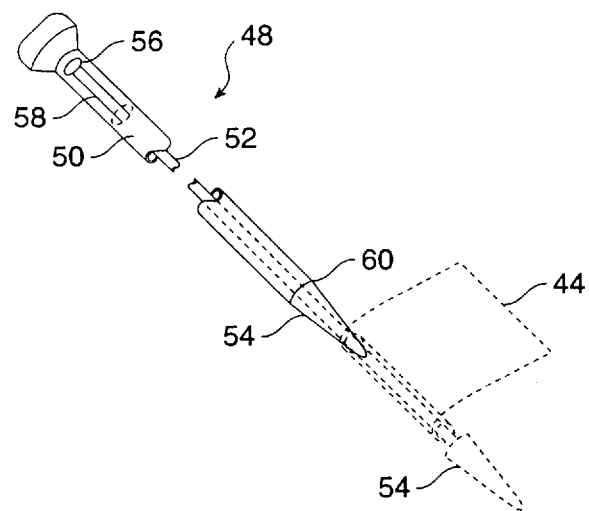
FIG. 3 illustrates a second embodiment of an introducer shaft constructed in accordance with the principles of the present invention.

A second embodiment of an introducer for use in the methods and systems of the present invention is illustrated in FIG. 3. The introducer 48 comprises a tubular shaft 50 having a rod 52 disposed in a lumen thereof. The tapered distal tip 54 secured to a distal end of the rod 52, and the rod 52 may be axially translated by sliding a button 56 in a slot 58 formed near the proximal end of the tubular shaft 50. When extended (as shown in broken line in FIG. 3) the distal tip 54 is axially spaced apart from the distal end 60; of the tubular shaft 50, thus creating an opening for placing an article, such as surgical mesh 44 in the annular space between the rod 52 and the interior of the tubular shaft 50. For example, the surgical mesh 44 may be wrapped around the rod 52 in a manner similar to that described in connection with introducer 36. The mesh 44 may then be drawn back to within the tubular shaft 50. This embodiment thus has the advantage that the surgical mesh 44 or other article being carried is protected by the tubular shaft as it is introduced through the conformable sleeve. It has the disadvantage, however, that the use of a separate shaft will generally increase the size of the introducer needed for introducing any given article.

Figure 4:
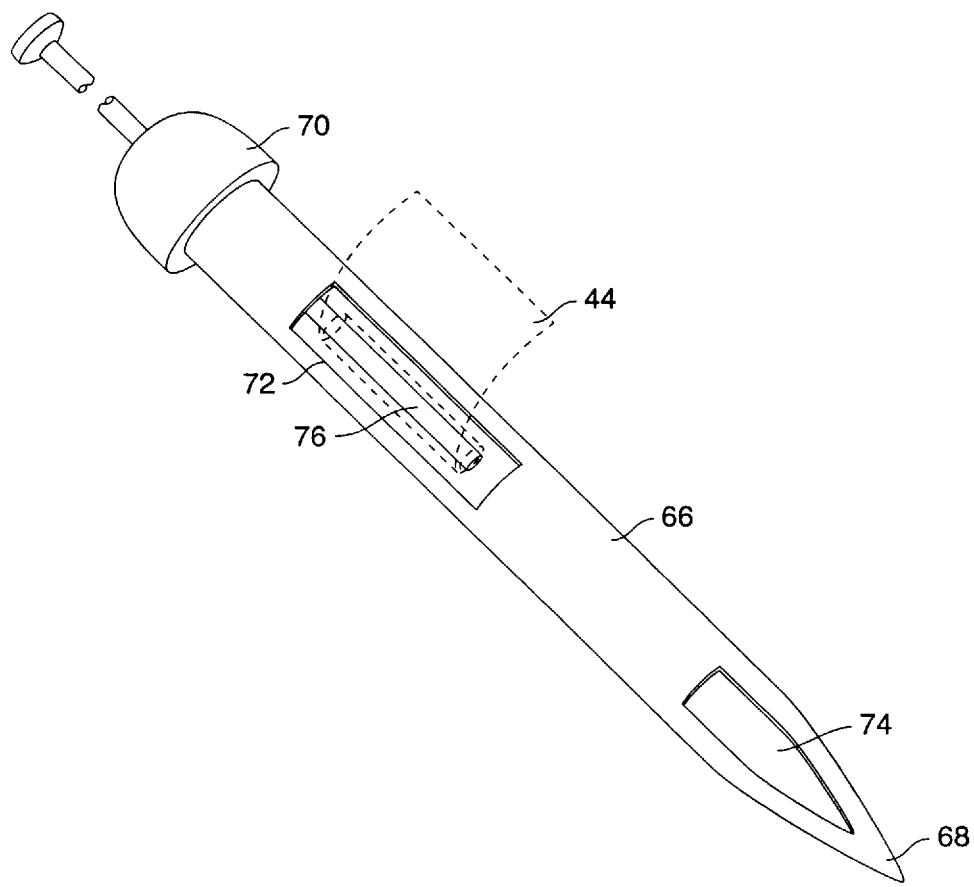
FIG. 4 illustrates a third embodiment of an introducer shaft constructed in accordance with the principles of the present invention.
Figure 4A:
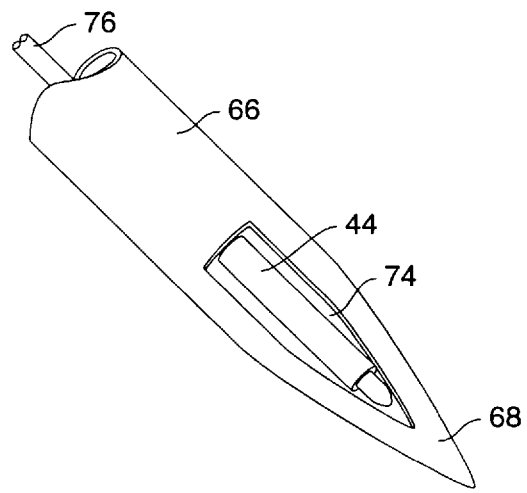
FIG. 4A is a detailed view of the distal end of the introducer shaft of FIG. 4.

A third embodiment of an introducer suitable for use in the methods and systems of the present invention is illustrated in FIGS. 4 and 4A. The introducer 64 comprises a tubular shaft 66 having a tapered distal tip 68 and a proximal handle 70. A first slot 72 is provided in the tubular shaft near the proximal handle, and a second slot 74 is provided in the tubular shaft near the tapered distal end 68. A rotatable rod 76 is slidably mounted within the handle so that it may be disposed adjacent the first slot 72 to permit mounting of the surgical mesh 44 through said first slot 72. This may be accomplished by spinning the rod in order to roll up the mesh. After the mesh has rolled onto the rod 76, the rod may be advanced in a distal direction so that the mesh is adjacent the second opening 74. After introduction through the conformable sleeve 10, the second slot 74 will be disposed within the target body cavity, and the mesh may be withdrawn using separate grasping instruments.

Figure 5A:
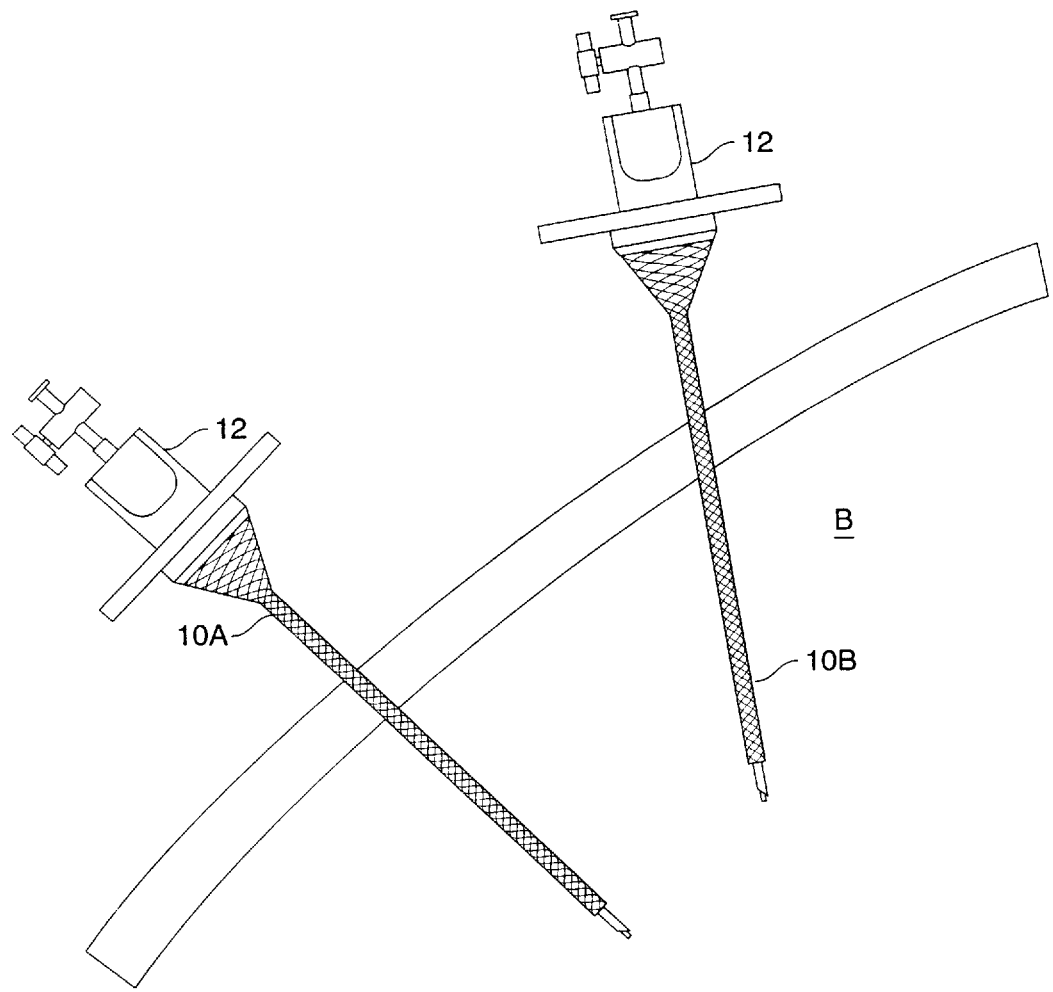
FIGS. 5A–5C illustrate use of the shaft of FIG. 2 for introducing an article and a surgical instrument through conformable sleeves according to the method of the present invention.
Figure 5B:
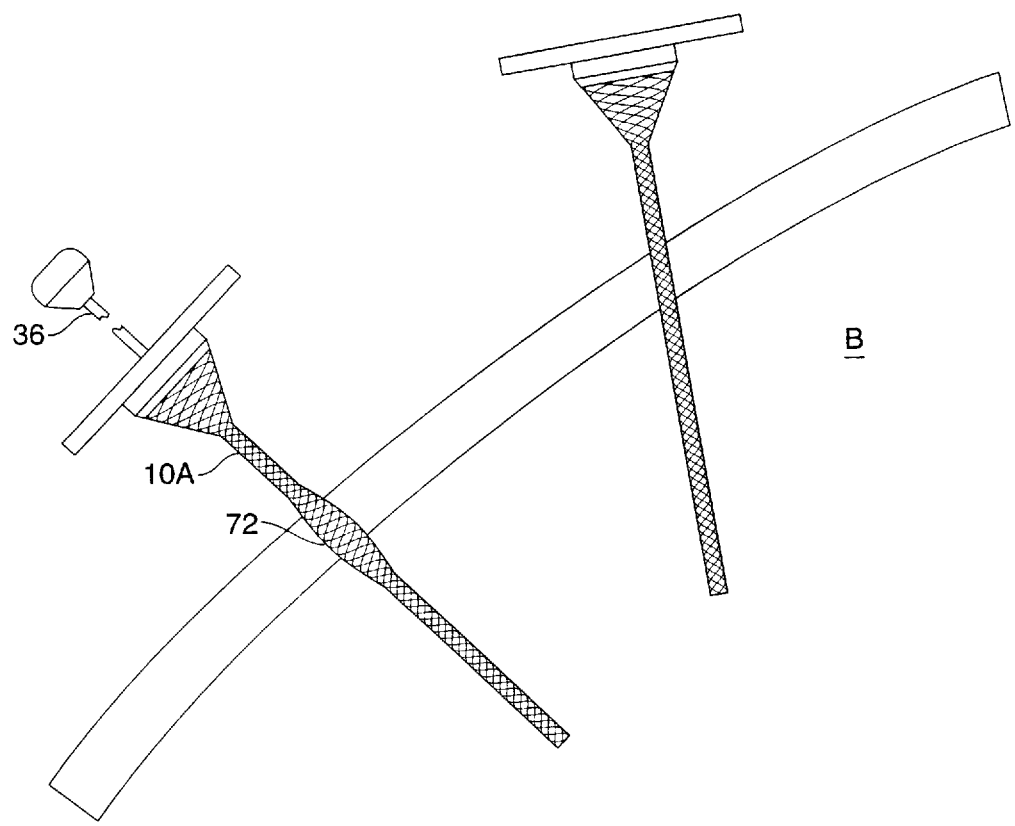
Figure 5C:
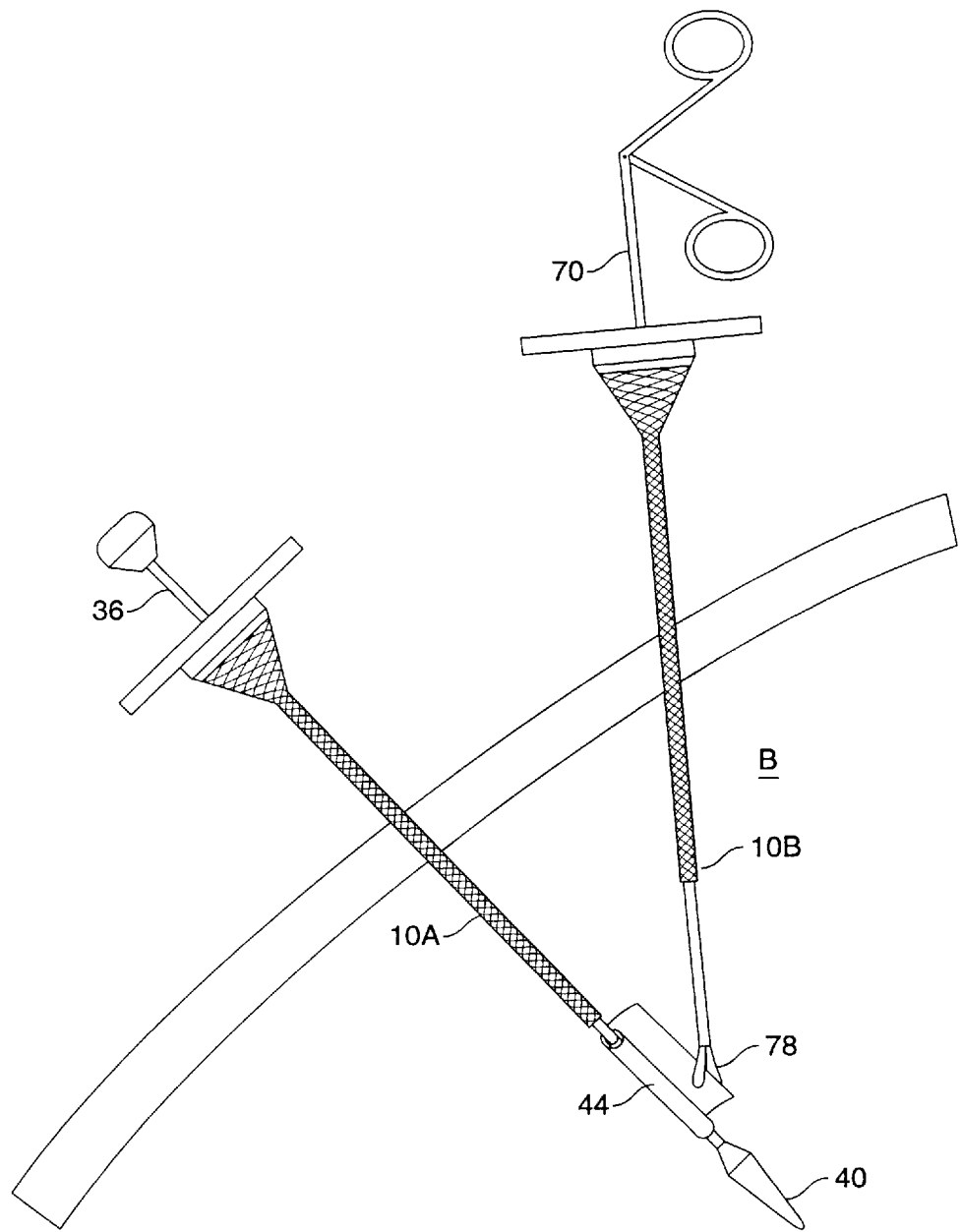

Referring now to FIGS. 5A–5C, use of the conformable sleeve 10 for introducing an article and a surgical instrument will be described. In particular, a first conformable sleeve 10A will be used together with a introducer 36 for introducing a surgical mesh 44 into a target body cavity B, and a second conformable sleeve 10B will be used for introducing surgical graspers 71 into the body cavity for removing the surgical mesh from the introducer 36. As shown in FIG. 5A, the first conformable sleeve 10A and second conformable sleeve 10B may be self-introduced using internally mounted pneumoperitoneum needles 12, as described above. The locations of the tissue penetrations formed are chosen so that the distal ends of the sleeves will be adjacent each other to permit removal of the surgical mesh 44 as described below.

After the conformable sleeves 10A and 10B are in place, the pneumoperitoneum needles 12 will be removed as shown in FIG. 5B. The introducer 36 is then used to pass the surgical mesh 44 through the first conformable sleeve 10A. As the introducer 36 progresses inwardly, the distal tip 40 will cause a bulge 73, as shown in FIG. 5B. Generally, the dimensions of the bulge will be just sufficient to accommodate the distal tip, and will usually be less than required for placement of a rigid cannula.

After the introducer 36 is passed fully inwardly, as shown in FIG. 5C, the surgical mesh 44 will be exposed within the interior of the body cavity B. The grasper 71 may then be introduced through the second conformable sleeve 10B, also as shown in FIG. 5C. The grasper 71 may be conventional laproscopic graspers having the length sufficient to pass through the sleeve 10B and a relatively low profile, i.e. narrow width. The graspers 71 may be positioned axially through the conformable sleeve 10B and may be moved about the point of percutaneous insertion in order to position the jaw 78 of the graspers adjacent the surgical mesh 44. An edge of the surgical mesh may then be grasped by the jaws 78, and the graspers manipulated to remove the mesh from the introducer 36. The schematic illustration of jaws 78 is intended to also serve as a symbolic representation for a variety of other end effectors which may be introduced through the conformable sleeve 10A, such as scissors, forceps, needle drivers, electrosurgical probes, staplers, viewing scopes, irragation devices, suction devices, and the like. The introducer 36 may then be withdraw outwardly through the conformable sleeve 10A. The graspers 71 may then be used to position the surgical mesh at the desired location for performing the intended procedure, typically hernia repair. The conformable sleeve 10A could then be withdrawn, or alternatively be used for introducing additional, other articles, or other instruments for performing the procedure.

In some instances, it may be desirable to utilize either of the conformable sleeves 10A or 10B for introducing a rigid cannula using the STEP™ system available from Innerdyne Medical. It would also be possible to utilize a conformable sleeve which has been initially placed as part of the STEP™ system, i.e. with a rigid cannula in the lumen thereof, for use in the methods of the present invention. In such cases, the rigid cannula should be removed from the conformable sleeve, allowing the sleeve to radially collapse. A desired introducer, article, surgical instrument, or the like, can then be introduced through the conformable sleeve according to the methods of the present invention.

Referring now to FIG. 6, an exemplary tapered carrier 80 will be described. The tapered carrier 80 comprises a cylindrical body 82 having a tapered, conical distal end 84. A grasping element 86 extends distally from the distal end of the tapered section 84. A surgical mesh 44, or other article, may be introduced through an opening 88 at the proximal end of the cylindrical body 82. Usually, the tapered carrier will be rigid. Alternatively, the carrier could comprise a collapsible structure which conforms to the shape of any article therein as the carrier is drawn through the conformable sleeve.

Figure 7A:
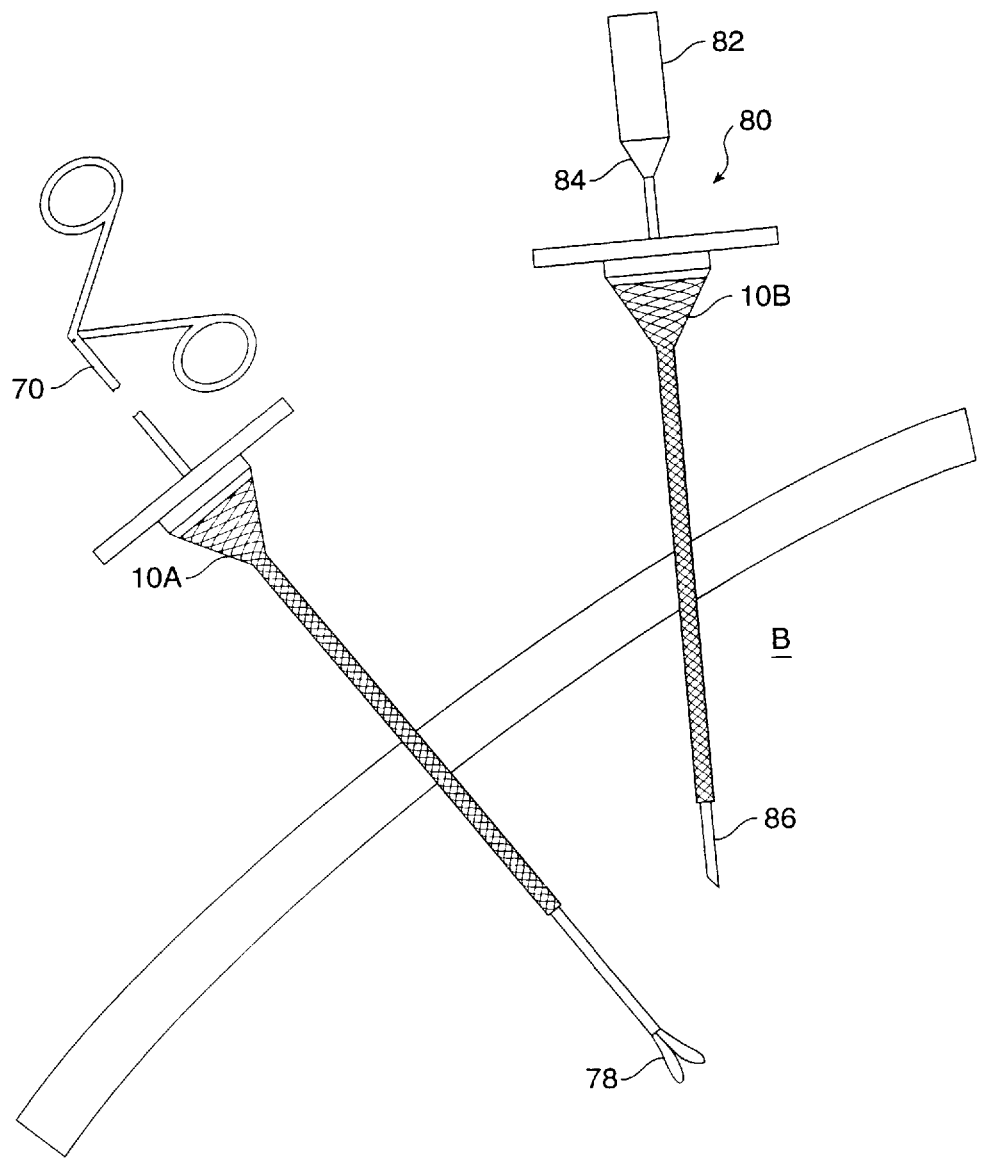
FIGS. 7A and 7B illustrate use of the tapered carrier of FIG. 6 and surgical graspers for introducing an article according to the method of the present invention.
Figure 7B:
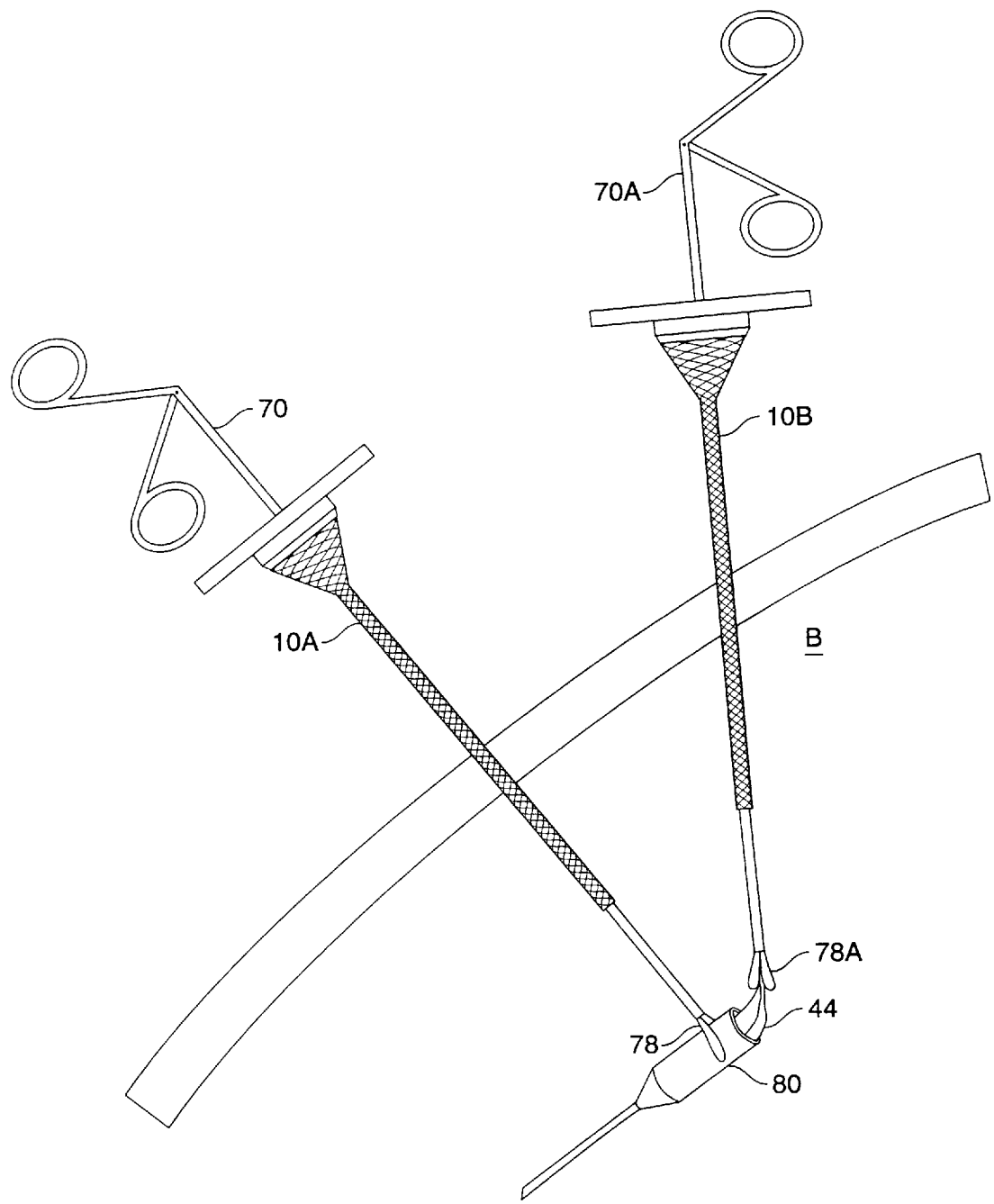

Referring now to FIGS. 7A and 7B, use of the conformable sleeves 10A and 10B positioned as described above with the tapered carrier 80 will be described. Initially, the graspers 71 are introduced through the conformable sleeve 10A and the tapered carrier is introduced through the second conformable sleeve 10B so that the grasping element 86 extends out of the distal end of sleeve 10B. Jaws 78 of the grasper 71 may then be manipulated to capture the grasping element 86 and draw the carrier 80 through the conformable sleeve 10B, as illustrated in FIG. 7B. Second surgical graspers. 71A may then be introduced through the conformable sleeve 10B and used to pull the surgical mesh 44 from the carrier 80, also as illustrated in FIG. 7B.

Figure 7C:
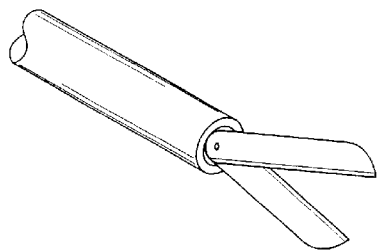
FIGS. 7C–J illustrate a variety of end effectors which may be introduced using the instruments and methods of the present invention.
Figure 7D:
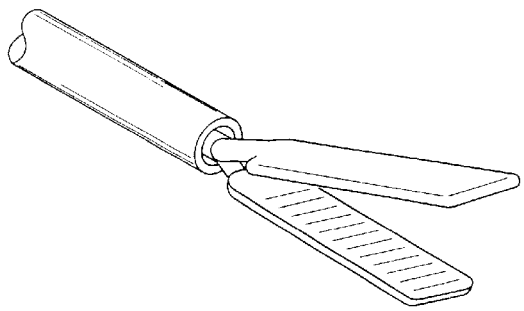
Figure 7E:
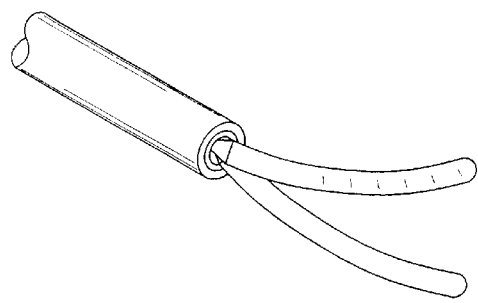
Figure 7F:
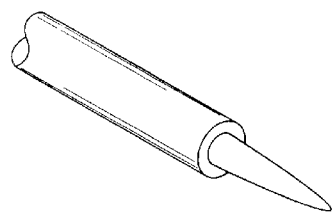
Figure 7G:
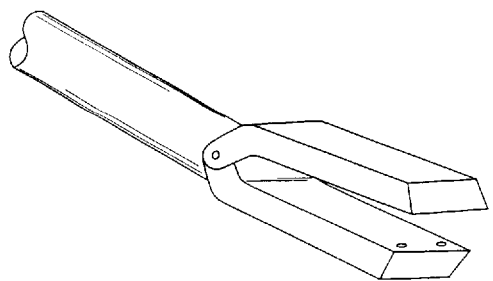
Figure 7H:
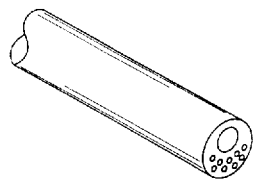
Figure 7I:
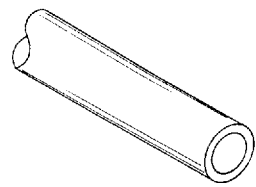
Figure 7J:
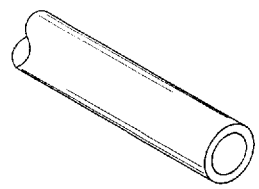

Instead of graspers 71, the conformable sleeve 10A can be used to introduce a number of other instruments having different end effectors. End effectors that may be introduced include scissors (FIG. 7C), forceps (FIG. 7D), needle drivers (FIG. 7E), electrosurgical probes (FIG. 7F), staplers (FIG. 7G), viewing scopes (FIG. 7H), irrigators (FIG. 7I), suction devices (FIG. 7J), and the like.

Although the foregoing invention has been described in some detail by way of illustration and example, for purposes of clarity of understanding, it will be obvious that certain changes and modifications may be practiced within the scope of the appended claims.

What is claimed is:

1. A method for percutaneously introducing an article, said method comprising:

percutaneously inserting a conformable sleeve to a target site in a body cavity;

passing an article from outside the body and through a lumen of the conformable sleeve, wherein passage of the article radially expands the lumen as the article advances; and grasping the article with graspers and pulling the article away from the sleeve with the graspers into the body cavity.

2. A method as in claim 1, wherein the passing step comprises:

mounting the article on a shaft; and introducing the shaft and article through the conformable sleeve so that said article extends from the sleeve into the body cavity.

3. A method as in claim 2, further comprising withdrawing the shaft from the conformable sleeve after the article has been removed, wherein the sleeve radially collapses.

4. A method as in claim 2, wherein the mounting step comprises storing the article in a recess on the shaft.

5. A method as in claim 4, wherein the recess is disposed proximal to a tapered distal end of the shaft.

6. A method as in claim 5, wherein the recess is covered by a cover and the article is removed through an aperture in the cover.

7. A method as in claim 5, wherein the recess is covered by a cover and the removing step comprises retracting the cover to expose the article in the body cavity.

8. A method as in claim 1, wherein the grasting step comprises:

percutaneously inserting a grasping element into the body cavity;

grasping the article with a distal end of the grasping element; and pulling the grasping element away from the conformable sleeve to draw the article into the body cavity.

9. A method as in claim 8, wherein the article is disposed in a tapered carrier and wherein a tapered end of the carrier is grasped by the grasping element and pulled through the conformable sleeve and the carrier is drawn into the body cavity.

10. A method as in claim 9, further comprising removing the article from the tapered carrier after the tapered carrier has been drawn into the body cavity.

11. A method as in claim 1, wherein the article has a non-circular cross-sectioned periphery so that the conformable sleeve is radially expanded to a non-circular cross-section as the article passes.

12. A method for performing a procedure at a target site in a body cavity, said method comprising:

percutaneously inserting a conformable sleeve to the target site;

positioning an elongate instrument through a central lumen of the conformable sleeve so that an end effector at a distal end of the instrument is positioned at the target site and a handle at a proximal end of the instrument remains outside the body; and manipulating the handle to deploy the end effector to perform the procedure.

13. A method as in claim 12, wherein the manipulating step comprises actuating an actuator on the handle to deploy the end effector.

14. A method as in claim 13, whereas the end effector comprises a component selected from the group consisting of graspers, scissors, forceps, needle drivers, electrosurgical probes, staplers, viewing scopes, irrigation devices, and suction devices.

15. A method as in claim 14, wherein the end effector comprises graspers and the method further comprises manipulating a proximal handle on the graspers to grasp and remove a surgical mesh from a second instrument and to place said mesh over tissue.

16. A method as in claim 12, wherein the manipulating step comprises translating the handle to engage the end effector against tissue in the body.

17. A system for percutaneously introducing an article, said system comprising:

an elongate introducer having a proximal end, a distal end, and a storage location near the distal end for removably carrying the article; and an elongate conformable sleeve having a proximal end, a distal end, and a lumen which slidably receives the introducer shaft, said sleeve having a compliant or elastic structure so that its cross-section will collapse when positioned in a constrictive percutaneous penetration but will expand as the introducer is passed through the lumen.

18. A system as in claim 17, wherein the introducer shaft has a tapered distal end to facilitate passage through the lumen of the elongate sleeve.

19. A system as in claim 18, wherein the storage location on the introducer shaft is recessed behind the tapered distal end.

20. A system as in claim 19, which introducer shaft includes a tubular cover over the storage location.

21. A system as in claim 20, wherein the tubular cover has an aperture for accessing the storage location.

22. A system as in claim 20, wherein the tubular cover retracts relative to the shaft.

23. A system as in claim 17, wherein the elongate sleeve has a length in the range from 5 cm to 20 cm and a maximum internal diameter when radially expanded in the range from 1 mm to 18 mm.

24. A system as in claim 23, wherein the introducer shaft has a length which is at least 5 cm longer than the elongate sleeve.

25. A system as in claim 17, further comprising the article carried within the storage location on the introducer shaft.

26. A system as in claim 25, wherein the article is a surgical mesh.

27. Apparatus for use in combination with an elongate conformable sleeve, said introducer shaft comprising:

a shaft having a proximal end and a distal end;

a tapered tip at the distal end of the shaft, said taper defining a recessed region on the shaft for receiving an article to be delivered by the shaft through the conformable sleeve; and a handle at the proximal end of the shaft.

28. Apparatus as in claim 27, wherein the shaft comprises a tubular cover which extends proximally from the tapered distal tip, wherein the recessed region is disposed within the cover.

29. Apparatus as in claim 28, wherein the tubular cover has an aperture for accessing the article.

30. Apparatus as in claim 28, wherein the tubular cover is retractable relative to the distal tip to expose the article.

31. Apparatus as in claim 27, shaft has a length in the range from 5 cm to 20 cm and a maximum width in the range from 5 mm to 18 mm.

32. A system for percutaneously introducing an article, said system comprising:
   a tapered carrier having a hollow body, tapered distal end, and an opening at the proximal end to permit loading and unloading of the article; and
   an elongate conformable sleeve having a proximal end, a distal end and a lumen which slidably receives the tapered carrier, said sleeve having an elastic or compliant structure so that its cross-section will collapse when positioned in a constrictive percutaneous penetration but will expand as the tapered carrier is passed through the lumen.

33. A system as in claim 32, wherein the elongate sleeve has a length in the range from 5 cm to 20 cm and a maximum internal diameter when radially expanded in the range from 5 mm to 18 mm.

34. A system as in claim 33, wherein the tapered carrier is non-collapsible.

35. A system as in claim 34, wherein the tapered carrier has a length in the range from 5 cm to 20 cm and a maximum width at its proximal end of from 5 mm to 18 mm.

36. A system for percutaneously introducing an article, said system comprising:
   an elongate introducer having a proximal end, a distal end, a storage location near the distal end for removably carrying the article, and a tubular cover over the storage location; and
   an elongate conformable sleeve having a proximal end, a distal end, and a lumen which slidably receives the introducer shaft, said sleeve having a compliant or elastic structure so that its cross-section will collapse when positioned in a constrictive percutaneous penetration but will expand as the introducer is passed through the lumen.

37. A system as in claim 36, wherein the introducer shaft has a tapered distal end to facilitate passage through the lumen of the elongate sleeve.

38. A system as in claim 37, wherein the storage location on the introducer shaft is recessed behind the tapered distal end.

39. A system as in claim 36, wherein the tubular cover has an aperture for accessing the storage location.

40. A system as in claim 36, wherein the tubular cover retracts relative to the shaft.

41. A system as in claim 36, wherein the elongate sleeve has a length in the range from 5 cm to 20 cm and a maximum internal diameter when radially expanded in the range from 1 mm to 18 mm.

42. A system as in claim 41, wherein the introducer shaft has a length which is at least 5 cm longer than the elongate sleeve.

43. A system as in claim 36, further comprising the article carried within the storage location on the introducer shaft.

44. A system as in claim 43, wherein the article is a surgical mesh.

45. A system for percutaneously introducing an article, said system comprising:
   an elongate introducer having a proximal end, a distal end, and a storage location near the distal end for removably carrying the article;
   an article removably carried within the storage location on the introducer shaft; and
   an elongate conformable sleeve having a proximal end, a distal end, and a lumen which slidably receives the introducer shaft, said sleeve having a compliant or elastic structure so that its cross-section will collapse when positioned in a constrictive percutaneous penetration but will expand as the introducer is passed through the lumen.

46. A system as in claim 45, wherein the introducer shaft has a tapered distal end to facilitate passage through the lumen of the elongate sleeve.

47. A system as in claim 46, wherein the storage location on the introducer shaft is recessed behind the tapered distal end.

48. A system as in claim 47, which introducer shaft includes a tubular cover over the storage location.

49. A system as in claim 48, wherein the tubular cover has an aperture for accessing the storage location.

50. A system as in claim 48, wherein the tubular cover retracts relative to the shaft.

51. A system as in claim 45, wherein the elongate sleeve has a length in the range from 5 cm to 20 cm and a maximum internal diameter when radially expanded in the range from 1 mm to 18 mm.

52. A system as in claim 51, wherein the introducer shaft has a length which is at least 5 cm longer than the elongate sleeve.

53. A system as in claim 45, wherein the article is a surgical mesh.

54. A system for percutaneously introducing an article, said system comprising:
   an elongate introducer having a proximal end, a distal end, and a recessed receptacle near the distal end for removably carrying the article; and
   an elongate conformable sleeve having a proximal end, a distal end, and a lumen which slidably receives the introducer shaft, said sleeve having a compliant or elastic structure so that its cross-section will collapse when positioned in a constrictive percutaneous penetration but will expand as the introducer is passed through the lumen.

55. A system as in claim 54, wherein the introducer shaft has a tapered distal end to facilitate passage through the lumen of the elongate sleeve.

56. A system as in claim 55, wherein the storage location on the introducer shaft is recessed behind the tapered distal end.

57. A system as in claim 56, which introducer shaft includes a tubular cover over the storage location.

58. A system as in claim 57, wherein the tubular cover has an aperture for accessing the storage location.

59. A system as in claim 57, wherein the tubular cover retracts relative to the shaft.

60. A system as in claim 54, wherein the elongate sleeve has a length in the range from 5 cm to 20 cm and a maximum internal diameter when radially expanded in the range from 1 mm to 18 mm.

61. A system as in claim 60, wherein the introducer shaft has a length which is at least 5 cm longer than the elongate sleeve.

62. A system as in claim 54, further comprising the article carried within the storage location on the introducer shaft.

63. A system as in claim 62, wherein the article is a surgical mesh.

* * * * *